US010214716B2

(12) United States Patent
Biksacky

(10) Patent No.: US 10,214,716 B2
(45) Date of Patent: Feb. 26, 2019

(54) METHOD AND APPARATUS FOR CONTINUOUS AUTOMATED PERFUSION SYSTEM HARVESTING FROM IN-SITU FILTRATION PROBE

(71) Applicant: Flownamics Analytical Instruments, Inc., Madison, WI (US)

(72) Inventor: Michael Biksacky, Madison, WI (US)

(73) Assignee: Flownamics Analytical Instruments, Inc., Madison, WI (US)

( * ) Notice: Subject to any disclaimer, the term of this patent is extended or adjusted under 35 U.S.C. 154(b) by 111 days.

(21) Appl. No.: 15/149,910

(22) Filed: May 9, 2016

(65) Prior Publication Data

US 2016/0326481 A1   Nov. 10, 2016

Related U.S. Application Data

(60) Provisional application No. 62/162,862, filed on May 18, 2015, provisional application No. 62/158,920, filed on May 8, 2015.

(51) Int. Cl.
| | |
|---|---|
| *C12M 1/34* | (2006.01) |
| *G01P 5/18* | (2006.01) |
| *C12M 1/00* | (2006.01) |
| *G01F 1/708* | (2006.01) |

(52) U.S. Cl.
CPC ............ *C12M 41/00* (2013.01); *C12M 29/04* (2013.01); *C12M 29/10* (2013.01); *G01F 1/708* (2013.01); *G01P 5/18* (2013.01)

(58) Field of Classification Search
None
See application file for complete search history.

(56) References Cited

U.S. PATENT DOCUMENTS

| | | | |
|---|---|---|---|
| 3,482,450 A | 12/1969 | Harris et al. | |
| 3,498,316 A | 3/1970 | Humphrey et al. | |
| 3,668,936 A | 6/1972 | Herron | |
| (Continued) | | | |

FOREIGN PATENT DOCUMENTS

| | | |
|---|---|---|
| EP | 0848242 A2 | 6/1998 |
| WO | 03093323 A9 | 4/2004 |

OTHER PUBLICATIONS

"International Search Report and Written Opinion of the International Searching Authority," dated Aug. 11, 2016 for PCT/US2016/031487 filed May 9, 2016.

*Primary Examiner* — Paul West
*Assistant Examiner* — Mark A Shabman
(74) *Attorney, Agent, or Firm* — Boardman & Clark LLP

(57) ABSTRACT

An apparatus and method for determining fluid flow (e.g., sterile media flow, filtrate flow, etc.) through tubing is provided. The apparatus includes an air source, a flow valve, a first sensor, a second sensor, and a media tubing section extending between the first sensor and the second sensor. In operation, air from the air source is introduced by the flow valve into a fluid flow to create a lead line of fluid immediately following the introduced air. As the lead line of fluid passes each sensor, the sensors are used to determine a time between when the lead line passes the first sensor and the second sensor and that determined elapsed time is used, along with a determined volume of the media tubing section to determine the rate of flow of the fluid flow.

12 Claims, 9 Drawing Sheets

(56) References Cited

U.S. PATENT DOCUMENTS

| | | | |
|---|---|---|---|
| 3,693,436 A * | 9/1972 | Gildner | G01F 1/704 250/576 |
| 3,759,667 A | 9/1973 | Bannister et al. | |
| 3,970,097 A * | 7/1976 | Voellmy | G01F 1/704 137/1 |
| 3,974,697 A | 8/1976 | Speth et al. | |
| 3,990,312 A | 11/1976 | Koukol et al. | |
| 4,450,862 A * | 5/1984 | Hogan | A61C 1/0061 137/595 |
| 4,825,706 A * | 5/1989 | Bailey | G01F 1/00 73/202 |
| 5,004,538 A * | 4/1991 | Apfel | G01N 30/32 210/101 |
| 5,080,866 A | 1/1992 | Sweatman et al. | |
| 5,137,054 A | 8/1992 | Harper et al. | |
| 5,355,735 A * | 10/1994 | Miller | G01F 1/708 73/861.05 |
| 5,380,665 A | 1/1995 | Mintz et al. | |
| 5,487,313 A | 1/1996 | Johnson et al. | |
| 5,547,875 A | 8/1996 | Petty et al. | |
| 5,834,314 A | 11/1998 | Huang et al. | |
| 6,130,098 A | 10/2000 | Burns et al. | |
| 6,203,759 B1 | 3/2001 | Pelc et al. | |
| 6,289,714 B1 | 9/2001 | Tartre et al. | |
| 6,432,721 B1 | 8/2002 | Zook et al. | |
| RE38,281 E | 10/2003 | Tisone | |
| 6,689,621 B2 | 2/2004 | Merten et al. | |
| 6,706,535 B2 | 3/2004 | Sacks et al. | |
| 7,059,352 B2 | 6/2006 | Bohm | |
| 7,156,117 B2 | 1/2007 | Bohm | |
| 8,549,934 B2 | 10/2013 | Biksacky et al. | |
| 2002/0141903 A1 | 10/2002 | Parunak et al. | |
| 2002/0156589 A1 | 10/2002 | Fematt et al. | |
| 2002/0192113 A1 | 12/2002 | Uffenheimer et al. | |
| 2003/0230486 A1 | 12/2003 | Chien et al. | |
| 2004/0109386 A1 | 6/2004 | Gold et al. | |
| 2004/0178917 A1 | 9/2004 | Duan et al. | |
| 2004/0232080 A1 | 11/2004 | Neyer et al. | |
| 2005/0109410 A1 | 5/2005 | Gilbert et al. | |
| 2005/0161112 A1 * | 7/2005 | Ehwald | B01L 3/502738 141/130 |
| 2005/0220629 A1 | 10/2005 | Bohm et al. | |
| 2008/0295590 A1 | 12/2008 | Sukegawa et al. | |
| 2008/0302178 A1 | 12/2008 | Karg et al. | |
| 2011/0027875 A1 | 2/2011 | Cathcart et al. | |
| 2014/0033834 A1 | 2/2014 | Biksacky et al. | |
| 2014/0096599 A1 | 4/2014 | Münch et al. | |

\* cited by examiner

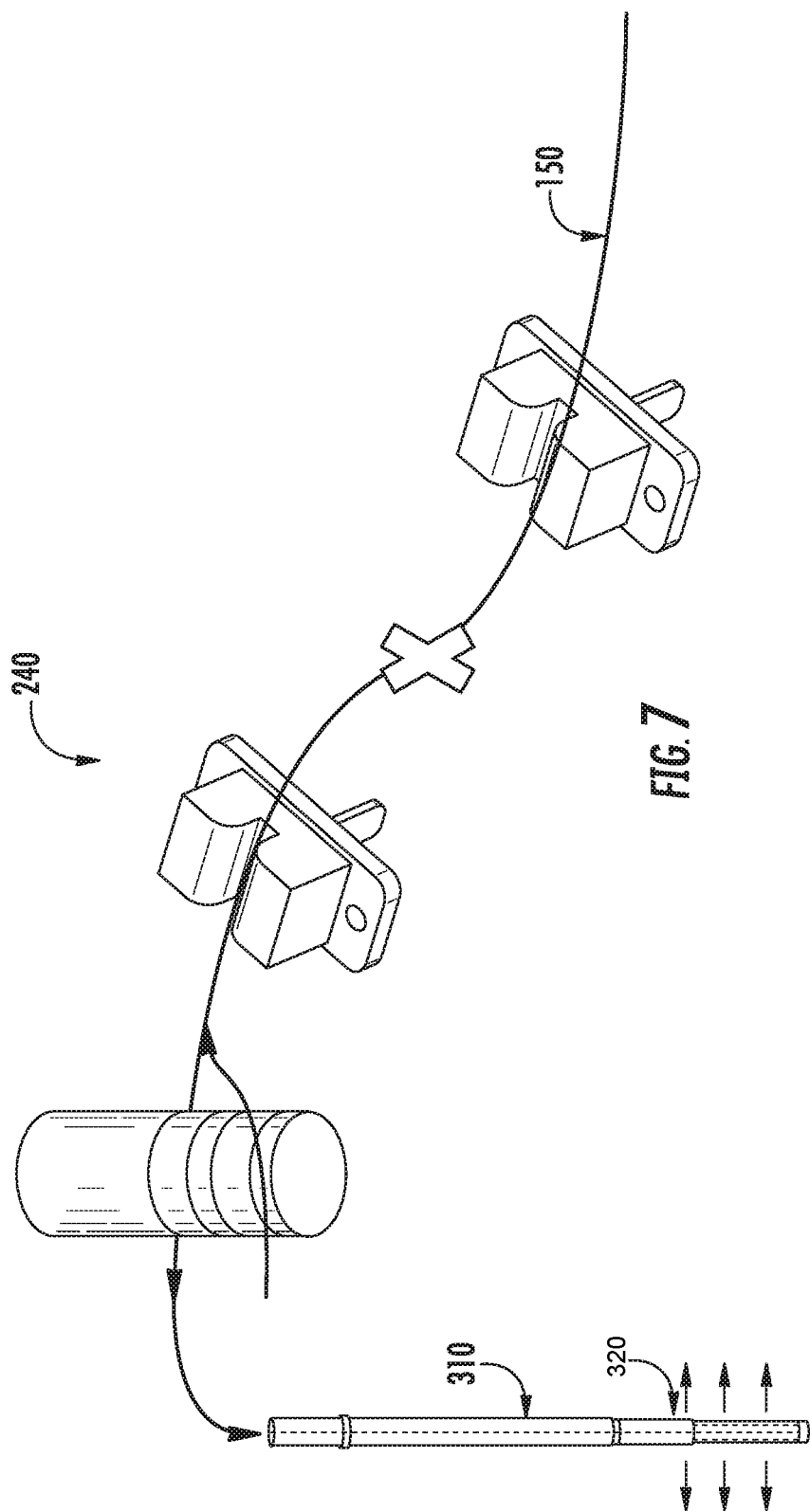

METHOD AND APPARATUS FOR CONTINUOUS AUTOMATED PERFUSION SYSTEM HARVESTING FROM IN-SITU FILTRATION PROBE

RELATED APPLICATIONS

This application claims priority to U.S. Provisional Patent Application Ser. No. 62/158,920, filed May 8, 2015, entitled "Method & Apparatus for Continuous Automated Perfusion System Harvesting from In-situ Filtration Probe," and U.S. Provisional Patent Application Ser. No. 62/162,862, filed May 18, 2015, entitled "Method and Apparatus for Sampling, Analysis, and Monitoring of (Tangential Flow) Filtration, Continuous Processing and Perfusion Systems," the entirety of each of which is hereby incorporated by reference herein.

FIELD

The present apparatus and methods relate to the field of pharmaceutical development, continuous bioprocessing and chemical or biochemical production, specifically filtrate removal and media addition related to filtration, cell generation, cell banking, cell culture seed expansion, cell harvest, media exchange and fluid clarification. The present apparatus and methods are more specifically related to the operation of retaining cells in a bioreactor while providing fresh nutrient containing media and removing the supernatant product containing filtrate.

BACKGROUND

Continuous bioprocessing is a method for pharmaceutical, chemical and biochemical production which limits the amount of intermediary steps and processes of more traditional methods. Traditional methods (such as batch processing) of pharmaceutical, chemical and biochemical production require moving batch fluids incrementally as a bolus from one process step to the next. Continuous bioprocessing is a means to decrease the frequency of mass fluidic transfer as well as reduce the separate equipment and space requirements. Generally, these processes involve controlled chemical or biological reactions occurring in a "bioreactor" which produce a specific product or products.

These reactions can take place from one day up to ninety days or longer. Traditional perfusion systems rely on devices to separate the cells from the supernatant media outside of the bioreactor; these include but are not limited to gravity settlers, sonic cell settlers, and centrifugation. More widely used forms of perfusion systems include but are not limited to alternating tangential flow filtration and tangential flow filtration. Such other devices require the cell containing fluid to be removed from the bioreactor where the cell separation occurs. This requires that the bioreactor will not contain all of the relevant fluids at any one point in time, and all of the fluid must transfer regularly between the bioreactor and a filtration apparatus.

Other known perfusion systems include spin filters. However, such systems are limited in their control capabilities, drivers, circuitry, etc.

SUMMARY

There is a need for an improved perfusion system and improvements over existing systems. For example, there is a need to an improved filtration probe to obtain the cell free sample and filter out cells and debris from a reactor before removing media from a tank, thus leaving substantially, if not all, of the cells in the reactor. There is also a need for a system and method which include a means of in-situ (inside the bioreactor) filtration that is controlled by a user interface and/or control module.

There is also a need for a system and method for monitoring the condition and observed flow rate leaving the filtration probe, and allowing a user to view flow performance during the process. There is also a need for a system and method for a system and method for back-flushing the filtration probe or membrane of the filtration probe as the observed flow rate from or through the filtration probe decreases or slows beyond acceptable or otherwise predetermined levels.

There is also a need for a system and method for detecting and auto calibrating flow rates based on user-defined settings and calibration intervals. There is also a need for a system and method including a controller for automating media addition and/or filtrate removal.

There is also a need for a system and method including a controller including a built-in PC and user interface touch screen which allows the user to set flow rates and calibration times locally at the machine. There is also a need for a system and method including a controller that may also be put on-line and accessed through a networked web-interface, meaning the user can control the system remotely (e.g., from outside of a lab).

There is also a need for a system and method configured with multiple sensors to help the system and method auto calibrate its flow rates.

Because typical perfusion systems remove a substantial portion of the reactor volume for cell separation, they are limited on the necessary minimum working volume (e.g., one liter). As such, there is also a need for a system and method that may be utilized to automate perfusion for much smaller reactor working volumes (e.g., as low as 250 mL, or less) than known systems.

There is also a need for a system and method for detecting and auto calibrating flow rates based on user-defined settings and calibration intervals. There is also a need for a system and method including a controller for automating media addition and/or filtrate removal.

The present disclosure is directed to a method and apparatus for monitoring fluid flow that works with multiple systems including perfusion and sampling systems, a system and method for monitoring the condition and observed flow rate leaving a filtration probe (or a dip tube, a sampling port, etc.), and allowing a user to view flow performance during the process. The present disclosure is also directed to a system and method for a system and method for back-flushing the filtration probe or membrane of the filtration probe as the observed flow rate from or through the filtration probe decreases or slows beyond acceptable or otherwise predetermined levels.

The present disclosure is directed to a method for monitoring flow, the method comprising: introducing an amount of air into a fluid flow; sensing, with a first sensor, a first time when a lead line of the fluid flow following the amount of air reaches the first sensor; sensing, with a second sensor, a second time when the lead line of the fluid flow reaches the second sensor; and using the first time and the second time to determine a flow rate for the fluid flow.

The present disclosure is also directed to an apparatus for monitoring flow, the apparatus comprising: a fluid path extending through a valve and past a first fluid sensor and a second fluid sensor; an air source extending through the valve and intersecting the fluid path between the valve and the first gas bubble sensor; and a control for controlling the valve to introduce a gas bubble into the fluid path to create a leading edge in fluid immediately following the gas bubble; a first sensor for sensing the leading edge of the fluid; a second sensor for sensing the leading edge of the fluid; and a timer for timing the elapsed time between the first sensor sensing the leading edge of the fluid and the second sensor sensing the leading edge of the fluid.

BRIEF DESCRIPTION OF DRAWINGS

Various examples of embodiments of the systems, devices, and methods according to this invention will be described in detail, with reference to the following figures, wherein:

FIG. 7 is a schematic diagram of a filtrate removal system and reactor of the perfusion system of FIG. 1 shown during filtrate back flush according to one or more examples of embodiments;

It should be understood that the drawings are not necessarily to scale. In certain instances, details that are not necessary to the understanding of the invention or render other details difficult to perceive may have been omitted. It should be understood, of course, that the invention is not necessarily limited to the particular embodiments illustrated herein.

DETAILED DESCRIPTION

Figure 1:
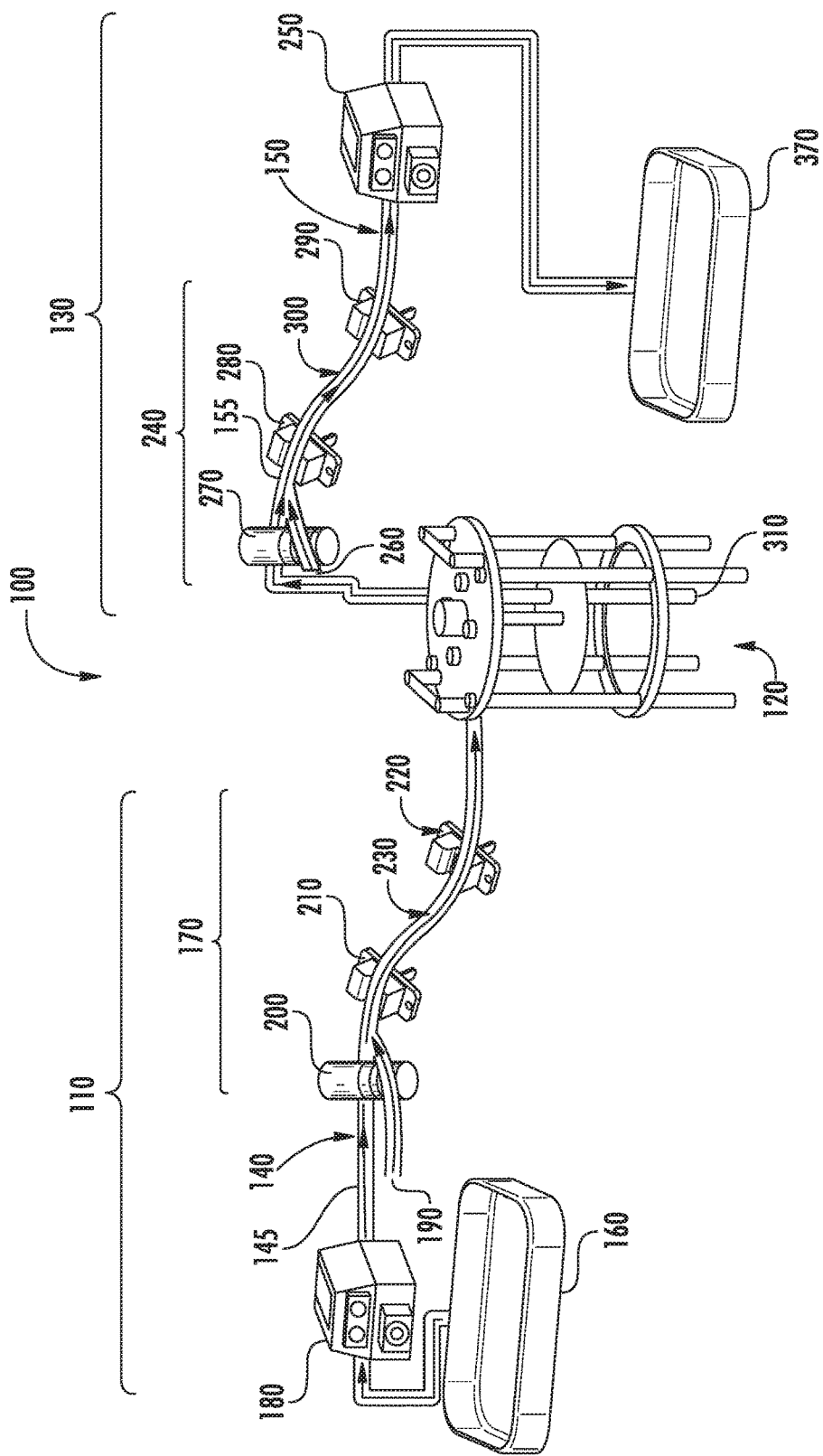
FIG. 1 is a schematic diagram of a perfusion system shown during media addition and filtrate removal, according to one or more examples of embodiments.

Referring to FIG. 1, a perfusion system 100 according to various examples of embodiments is shown. In various embodiments, the perfusion system is a continuous automated perfusion system for harvesting filtered media or a perfusion media removal (PMR) system. In various embodiments, perfusion system 100 includes a media addition system or stream 110, a reactor 120, and a filtrate removal system or stream 130. In various embodiments, the media addition system or stream 110, reactor 120, and filtrate removal system or stream 130 are fluidly coupled (e.g., via a media flow or fluid path 140 including tubing 145 and one or more connections, and a filtrate flow or fluid path 150 including tubing 155 and one or more connections). In various embodiments, apparatus includes one or more pumps which may be used for filtrate removal and sterile media addition, and calibrated by sterile air introduction on user defined intervals.

Figure 2:
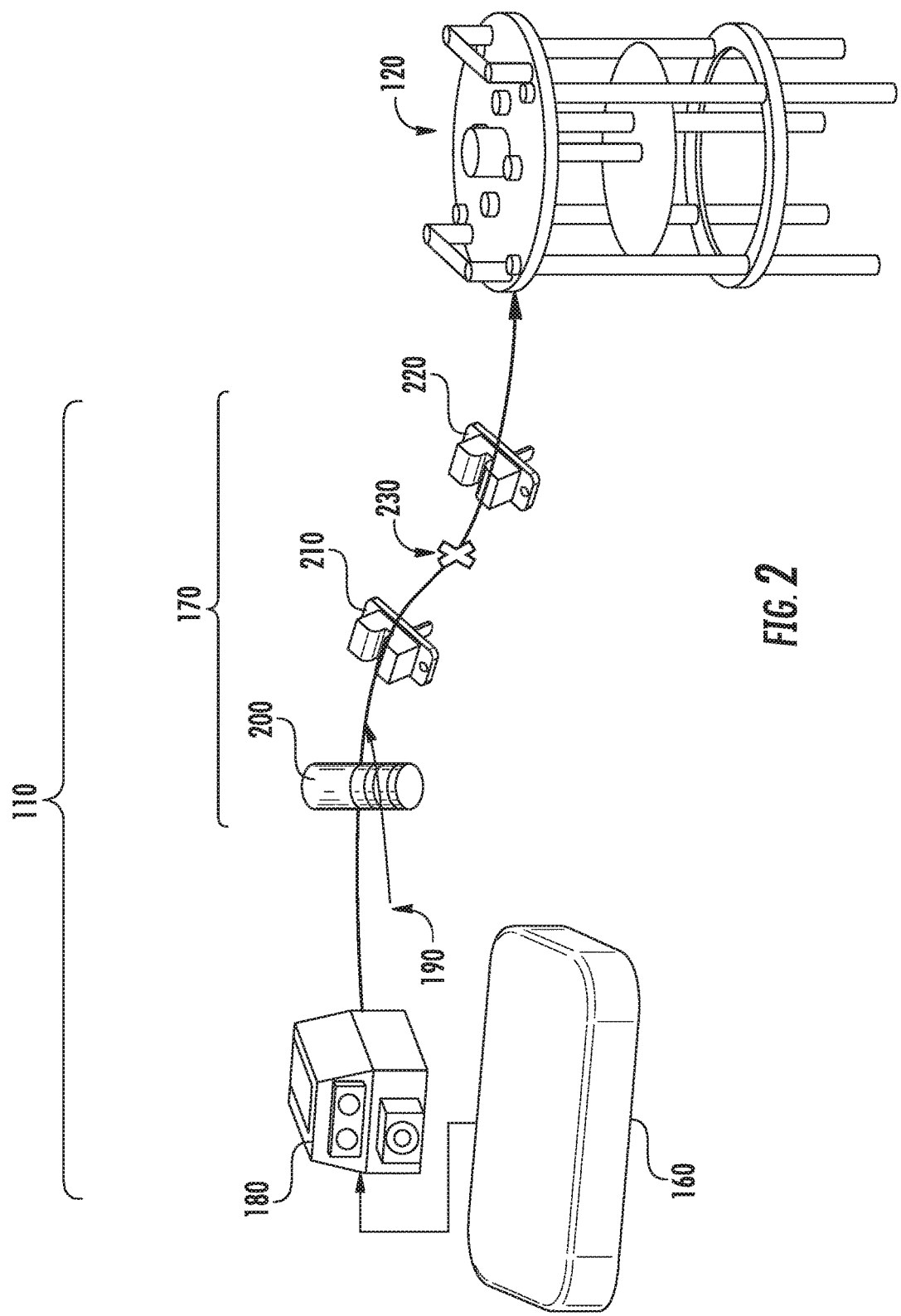
FIG. 2 is a schematic diagram of a media addition system and reactor of the perfusion system of FIG. 1 shown during media addition according to one or more examples of embodiments.

Referring now to FIGS. 1 and 2, in various embodiments, media addition system or stream 110 is configured or adapted to maintain a certain level, levels, flow or flows of media (e.g., sterile media) in or into reactor 120. In various embodiments, media addition system or stream 110 includes a media source (e.g., sterile media source) 160, and a dual fluid sensor media flow meter system, apparatus or device 170. In various embodiments, media addition system or stream 110 includes a media pump 180.

Figure 3:
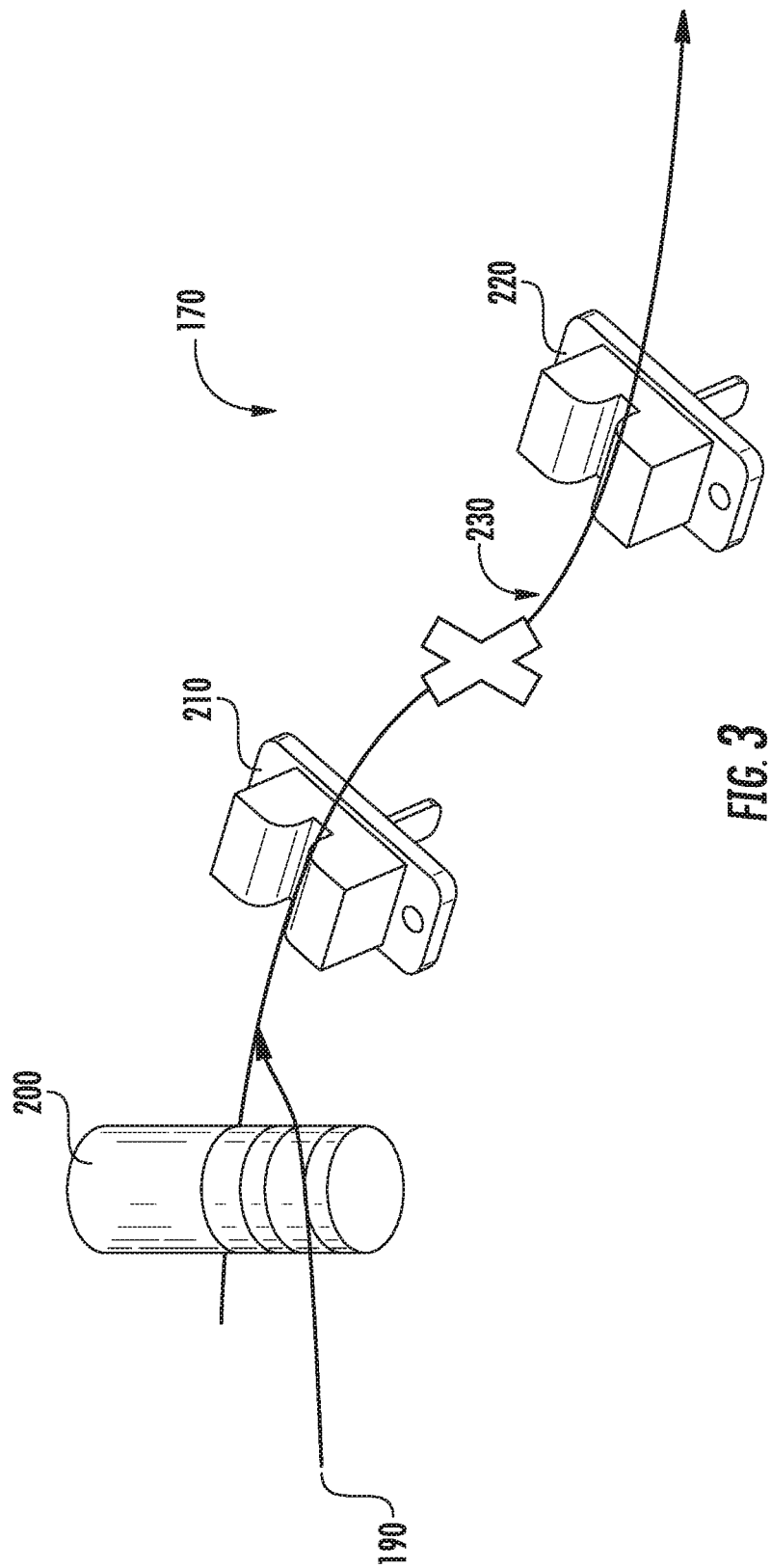
FIG. 3 is a schematic diagram of a dual fluid sensor flow meter apparatus or the media addition system of the perfusion system of FIG. 1 shown during media addition according to one or more examples of embodiments.

Referring now to FIGS. 1-3, in various embodiments, dual fluid sensor media flow meter system, apparatus or device 170 includes a media flow gas source 190 (e.g. a sterile or other air source), a media flow valve 200 (e.g., a dual pinch valve, solenoid valve, etc.), a first media sensor 210, a second media sensor 220, and a media tubing section 230 extending between the first media sensor 210 and the second media sensor 220.

In various embodiments, first media sensor 210 and/or second media sensor 220 are identical or similar type sensors. For example, in various embodiments, first media sensor 210 and/or second media sensor 220 are each bubble indicators. However, the first and second media sensors may also be other types of sensors such as fluid sensors. In various embodiments, first media sensor 210 and/or second media sensor 220 are self-calibrating. In various embodiments, one or more hardware controllers (not shown) are utilized to monitor first media sensor 210, second media sensor 220, and/or monitor and control media pump 180. In various embodiments, one or more user software interfaces (not shown) are utilized to define flow rates and/or calibration cycles of media addition system or stream 110.

In various embodiments, one or more components of media addition system or stream 110 are pre-sterilized (e.g., with gamma radiation and/or in an autoclave). Connections between components may be made with disposable tubing 145 and/or standard medical grade connectors.

Figure 4:
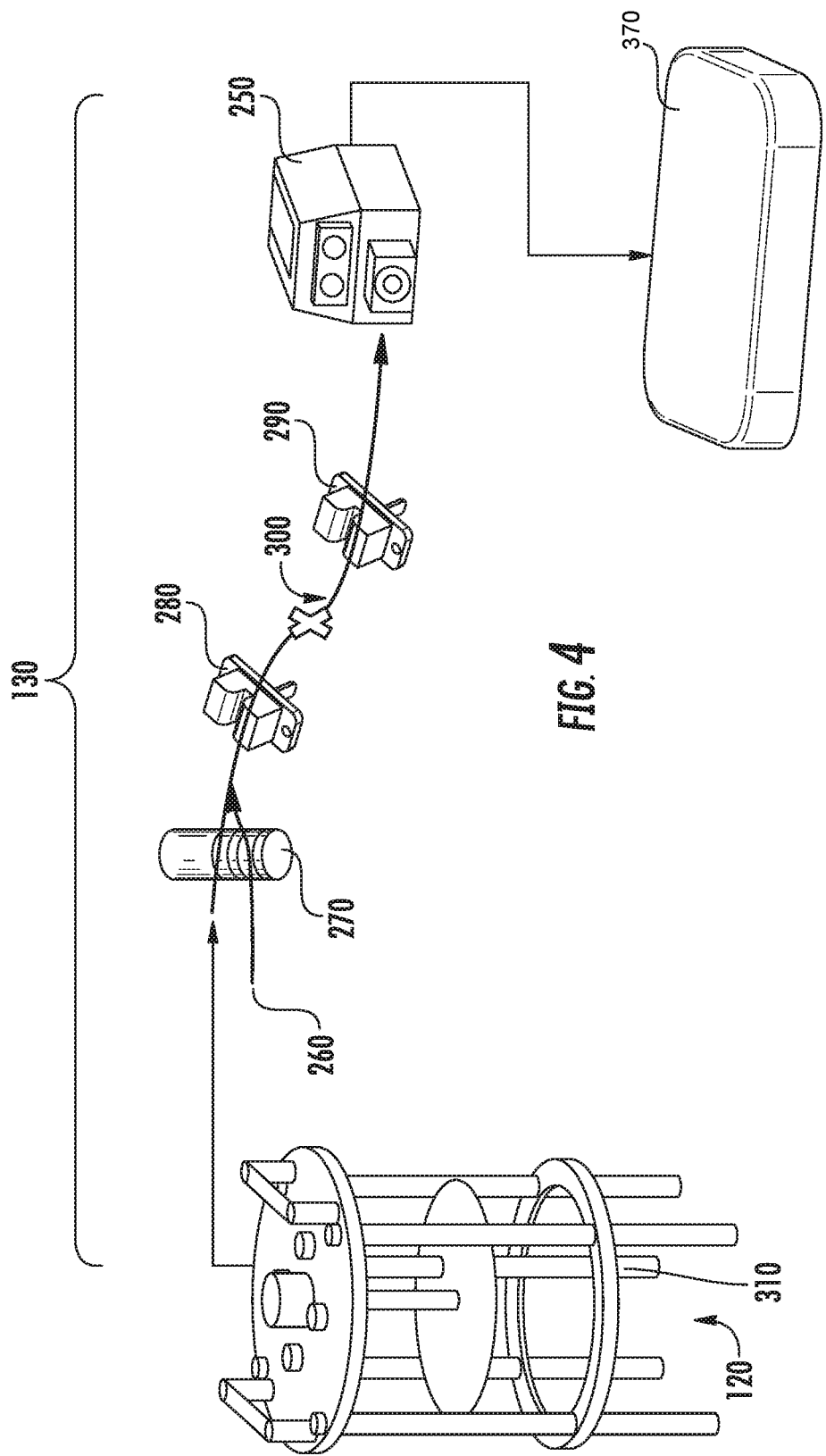
FIG. 4 is a schematic diagram of a filtrate removal system and reactor of the perfusion system of FIG. 1 shown during filtrate removal according to one or more examples of embodiments.

Referring now to FIGS. 1 and 4, in various embodiments, filtrate removal system or stream 130 is configured or adapted to remove filtrate or supernatant product containing fluid from reactor 120 and help maintain a certain level, levels, flow or flows of media (e.g., sterile media) out or from reactor 120. In various embodiments, filtrate removal system or stream 130 includes a dual fluid sensor filtrate flow meter system, apparatus or device 240. In various embodiments, filtrate removal system or stream 130 includes a filtrate pump 250.

In various embodiments, dual fluid sensor filtrate flow meter system, apparatus or device 240 includes an filtrate flow gas source 260 (e.g. a sterile or other air source), a filtrate flow valve 270 (e.g., a dual pinch valve, solenoid valve, etc.), a first filtrate sensor 280, a second filtrate sensor 290, and a filtrate tubing section 300 extending between the first filtrate sensor 280 and the second filtrate sensor 290.

In various embodiments, first filtrate sensor 280 and/or second filtrate sensor 290 are identical or similar type sensors. For example, in various embodiments, first media sensor first filtrate sensor 280 and/or second filtrate sensor 290 are each bubble indicators. However, the first and second filtrate sensors may also be other types of sensors such as fluid sensors. In various embodiments, first filtrate sensor 280 and/or second filtrate sensor 290 are self-calibrating. In various embodiments, one or more hardware controllers (not shown) are utilized to monitor first filtrate sensor 280, second filtrate sensor 290, and/or monitor and control filtrate pump 250. In various embodiments, one or more user software interfaces (not shown) are utilized to define flow rates and/or calibration cycles of filtrate removal system or stream 130.

In various embodiments, one or more components of filtrate removal system or stream 130 are pre-sterilized (e.g., with gamma radiation and/or in an autoclave). Connections between components may be made with disposable tubing 155 and/or standard medical grade connectors. According to various examples of embodiments, the output of filtrate removal pump 250 may be coupled to a sterile filtrate containment vessel 370 (product storage), or sent to an on-line or off-line fraction collector or instrument.

In various embodiments, the reactor includes any known or later developed lab, pilot production vessels which are useful for cell culture, fermentation, biochemical or chemical production, etc. (such as a bioreactor, a chemical processing vessel, a fermentation vessel, a process stream, a water treatment vessel, or similar perfusion reactor structure). In various embodiments, perfusion system 100 and, more specifically, filtrate removal system or stream includes an in-situ filtration probe 310 to help draw or for use in drawing filtrate out of reactor 120.

Figure 5:
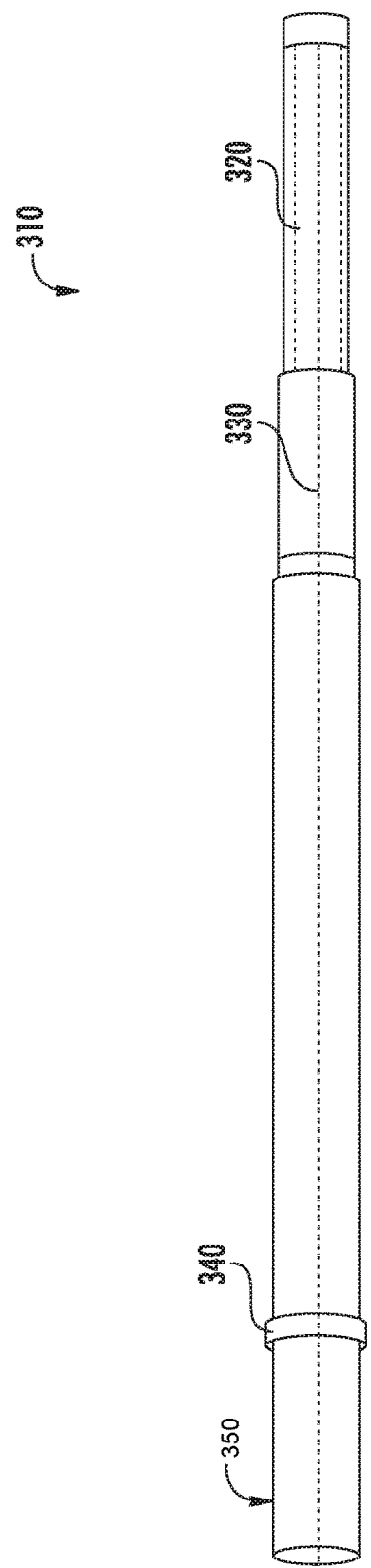
FIG. 5 is an isometric view of an in-situ filtration probe, according to various examples of embodiments.

Referring to FIG. 5, in-situ filtration probe 310 is shown according to various examples of embodiments, In various embodiments. in-situ filtration probe 310 includes a filtration membrane 320. In various embodiments, filtration membrane 320 blocks or prevents cells from entering an inner channel 330. In various embodiments, in-situ filtration probe 310 includes a reactor mounting flange 340. In various embodiments, reactor mounting flange 340 is adapted or configured to help retain in-situe filtration probe 310 relative to the reactor (e.g., retaining in-situ filtration probe 310 such that an external connection 350 is retained outside of a reactor head plate). in various examples, a. remainder of in-situ filtration probe 310 (e.g. a portion of in-situ filtration probe 310 extending between reactor mounting flange 340 and filtration membrane 320 is provided inside of the reactor. In operation, suction is generated at or about external connection 350 via tubing from the filtrate pump to help filter cells from the filtrate. In various embodiments, filtration membrane 320 of in-situ filtration probe 310 is made of a porous filter which is mounted externally to inner channel 330.

In-situ filtration probe 310 may filter cells in a variety of sizes. For example, in various embodiments, in-situ filtration probe filters cells ranging from 0.2 μm to 250 μm. The in-situ filtration probe may come in a variety of sizes and immersion lengths.

Figure 6:
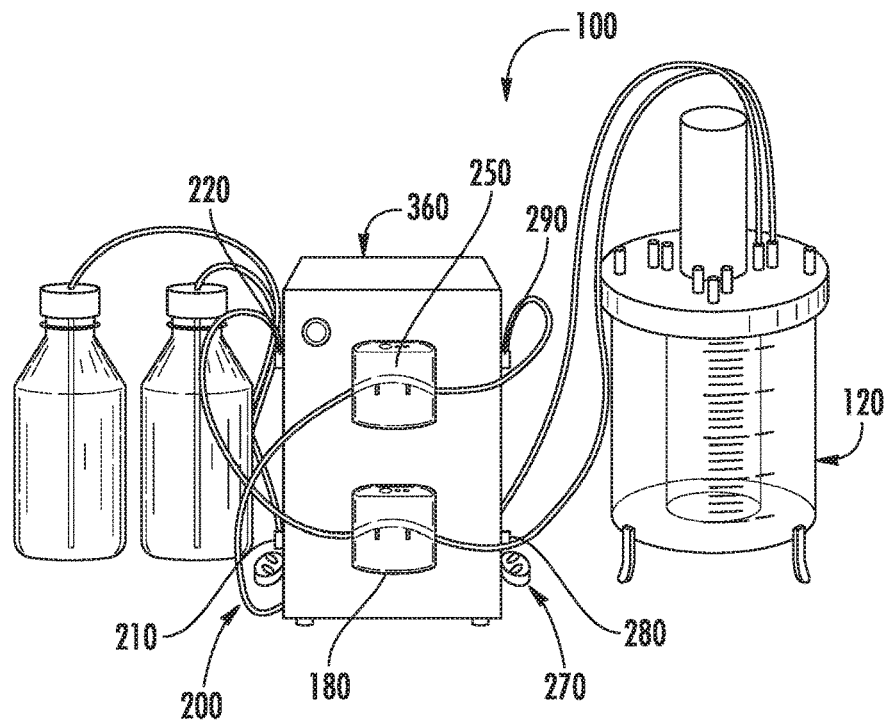
FIG. 6 is a perspective view of a perfusion system according to various examples of embodiments.

Referring now to FIG. 6, in various embodiments, a controller 360 helps monitor and/or control a flow meter (such as the dual fluid sensor media flow meter system, apparatus or device and/or the dual fluid sensor filtrate flow meter system, apparatus or device). For example, as shown in FIG. 6, in various embodiments, one or more media and filtrate pumps 180/250, media flow and filtrate flow valves 200/270, first and second media sensors 210/220 and/or first and second filtrate sensors 280/290 are coupled and controlled by a controller 360. For example, media and filtrate pumps 180/250, media flow and filtrate flow valves 200/270, first and second media sensors 210/220 and/or first and second filtrate sensors 280/290 may be coupled to a driver board which is coupled (e.g., to a communication cable coupled) to controller 360. In various embodiments, controller 360 powers media and filtrate pumps 180/250, media flow and filtrate flow valves 200/270, first and second media sensors 210/220 and first and second filtrate sensors 280/290 and includes the PC for the user interface.

Level sensors may be coupled to the reactor and critical values for these sensors may be controlled with the controller. The level sensors include, but are not limited to, ultrasonic, optical and capacitance sensors.

Also, the disclosed system may detect and auto-calibrate flow rates based on user-defined settings and calibration intervals. In addition, in various embodiments, the controller automates both media addition and filtrate removal, which is not currently accomplished by typical or known perfusion systems.

In various examples of embodiments, controller 360 controls the media addition system or stream (including media pump 180, first and second media sensors 210/220, and/or sterile connections thereof) and the filtrate removal system or stream (including in-situ filtration probe 310, first and second filtrate sensors 280/290, filtrate pump 250, and/or sterile connections thereof). In various embodiments, the controller includes a PC which has a user interface configured to help monitor, control and/or maintain various perfusion system parameters or settings including, but not limited to, the following:
    a. User defined addition and removal flow rates
    b. User defined calibration intervals
    c. Graphical or numerical representation of filtration probe flow rate
    d. Control of all pumps and valves
    e. Starting and Stopping the system
    f. Determining critical reactor levels
    g. Determining back flush intervals
    h. Bi-directional OPC Control In various embodiments, perfusion system 100 includes or is in communication with a user interface which may be used for, among other things, one or more of the following:
    a. Defining flow rates of harvest pump
    b. Defining flow rates of media addition
    c. Defining calibration cycles frequencies for peristaltic pumps
    d. Starting and stopping the system
    e. Determining critical reactor levels
    f. Determining back flush protocol Referring to FIG. 6, in various embodiments, controller 360 includes or is in communication with a PC and a user interface touch screen which allows a user to set flow rates and calibration times locally at the machine. The controller may also be put on-line and accessed through a networked web-interface, meaning the user can control the system remotely (e.g., from outside of a lab). Other components may be coupled via custom cables to the controller. The controller and/or user interface may have a touch screen, or be coupled via a web-interface network for user access, etc.

Referring again to FIG. 1, in operation, in various embodiments, one or more components, and flow or fluid paths 140/150 and connections are sterilized (e.g., irradiated or autoclaved). After sterilization, media flow or fluid path 140 and filtrate flow or fluid path can be run or provided through dual fluid sensor media flow meter system 110 and (e.g., provided in openings defined in first and second media sensor 210/220 and into media flow valve 200) and/or dual fluid sensor filtrate flow meter system 130 (e.g., provided in openings defined in first and second filtrate sensor 280/290 and into filtrate flow valve 270). A user may then boot up the system and utilize the user interface. The user may specify or set one or more of the filtrate removal and media addition flow rates, the interval at which filtrate pump 250 is running and the interval at which perfusion system 100 calibrates the specified filtrate removal and/or media addition flow rates. In various embodiments, the user has Start/Stop control (also can be triggered by OPC process triggering) to initiate and disable perfusion system 100. In various embodiments, perfusion system 100 controls media addition system or stream 110 and/or filtrate removal system or stream 130. When perfusion system 100 is started, media pump 180 and/or filtrate pump 250 introduce (e.g. by creating suction or draw) fluid into and/or through media flow or fluid path 140 and/or filtrate flow or fluid path 150 and, more particularly, dual fluid sensor media flow meter system, apparatus or device 170 and/or dual fluid sensor filtrate flow meter system, apparatus or device 240. In various embodiments, media addition system or stream 110 and filtrate removal system or stream 130 are independently controlled. In various embodiments, however, media addition system or stream 110 and filtrate removal system or stream 130 may be flowing at approximately the same rate to help maintain reactor volume.

In operation, the present apparatus and methods include a means of in-situ (inside the bioreactor) filtration which is controlled by a user interface and control module. For example, in various embodiments, the device used to obtain the cell free sample, in-situ filtration probe 150, is used to filter out cells and debris inside reactor 120 before removing media from reactor 120, thus leaving substantially all, if not all, of the cells in reactor 120. In various embodiments, this is accomplished by filtration using the porous membrane covering an in-situ shaft. In operation, in various embodiments, in-situ filtration probe 150 is used to retain cells in reactor 120 while allowing or helping filtrate pump 250 draw or otherwise introduce supernatant product containing fluid into filtrate removal system or stream 130. For example, suction may be generated through tubing from filtrate pump 250 (e.g., at the controller). According to various examples of embodiments, output from filtrate pump 250 may be directed to a containment vessel (e.g. sterile vessel for storage, collection, purification, or analysis), or sent to an on-line or off-line fraction collector or instrument. Filtrate removal system or stream 130 may be used to divert some or all filtrate to one or more online and offline analytical, storage and purification devices which include but are not limited to the following: HPLC and UPLC systems, fraction collectors, biochemistry analyzers, purification systems, storage vessels, etc.

In operation of various embodiments, addition of sterile media into reactor 120 through media addition system or stream 110 is controlled at least in part by media pump 180 which is controlled based on sensed or determined flow in a feedback loop or media tubing section 230 between first media sensor 210 and second media sensor 220. Media addition flow rates, as well as calibration intervals, may also be user- or pre-determined.

In various embodiments, media pump 180 is used to push, pull or otherwise draw or introduce media through dual sensor media flow meter system, apparatus or device 170 to calibrate media addition (e.g., based on user-defined intervals). In various embodiments, the media is drawn from media source 160, which is typically irradiated. It should be appreciated, however, that other ways of sterilizing or reducing the amount of contaminants may be utilized.

In various embodiments, in operation, filtrate removal system or stream 130 is monitored and/or controlled similarly to media addition system or stream 110, with the addition of in-situ filtration probe 310. In various embodiments, filtrate pump 180 is used to push, pull or otherwise draw or introduce media through in-situ filtration probe 310 and filtrate removal system or stream 130, including dual fluid sensor filtrate flow meter system, apparatus or device 240, to calibrate filtrate removal (e.g., based on user-defined intervals). In various embodiments, a dual fluid sensor filtrate flow meter system, apparatus or device 240 provides feedback for calibrating or recalibrating filtrate pump 250. In various embodiments, sensing and feedback from dual fluid sensor filtrate flow meter system, apparatus or device 240 allows the controller to adjust or compensate for membrane 320 fouling (e.g. reduced determined or observed flow rate over time at a consistent filtrate pump 250 setting). The feedback from dual fluid sensor filtrate flow meter system, apparatus or device 240 also allows the user interface to display, record, store, etc., fouling over time and allows the user to judge filtration performance.

In various embodiments, dual fluid sensor media flow meter system, apparatus or device 170 helps media addition system or stream 110 meet predetermined and/or user defined flow rates. For example, in various embodiments, first media sensor 200 and second media sensor 210 may be used to track movement through media flow or fluid path 140 in media addition system or stream 110. For example, in various embodiments, a length of the media tubing section 230 extending between first media sensor 210 and second media sensor 210 and/or an interior volume of the media tubing section 230 extending between first media sensor 210 and second media sensor 220 over that length may be known or determined, and utilized to determine real time flow rates. In various embodiments, media flow valve 200 may be operated to introduce or otherwise allow air from media flow gas source 190 into media flow or fluid path 140 and ultimately into media tubing section 230. In various embodiments, first media sensor 210 and second media sensor 220 can then each sense or read when a lead line of fluid following the introduced gas (e.g., air or sterile air) passes each of first media sensor 210 and second media sensor 220 and measure or otherwise determine the time that elapses from the moment each sensor 210 and 220 respectively senses the lead line of fluid following the introduced gas reaching or passing each sensor 210 and 220. By knowing the volume of media tubing section 230 extending between first media sensor 210 and second media sensor 220 (and/or the length of media tubing section 230 extending between first media sensor 210 and second media sensor 220), and the time elapsed between sensing of the lead line by first media sensor 210 and the sensing of the lead line by second media sensor 220, a flow rate may be determined, derived or at least approximated.

In operation, in various embodiments, dual fluid sensor media flow meter system, apparatus or device 170 allows or introduces one or more gas bubbles (e.g., air bubbles) into media flow or fluid path 140 through a sterile gas filter (e.g., by actuating media flow valve 200) and helps track the leading edge of the fluid (behind the gas bubble) as it passes each sensor 210 and 220. For example, in various embodiments, as the leading fluid edge passes first media sensor 210, a media timer is activated and as the leading fluid edge passes second media sensor 220, the media timer may be stopped and read. A known or measured inner diameter of media tubing section 230 and the length of media tubing section 230 between the first and second sensors 210/220 may be determined, fixed or known and correlate to or used to approximate or measure a volume (e.g., an interior volume). The resulting media timer may be used to determine the actual observed flow rate (e.g., x mL in y sec) and correlated to the media pump 180 setting used for that observed flow rate. Media pump 180 speed adjustments may be made to keep the observed flow rate at, or within a threshold of, a predetermined or user setting. Gas bubbles may later be purged from media flow or fluid path 140 if required or desired.

In various embodiments, perfusion system 100 helps maintain optimal reactor 120 volume by introducing sterile media by means of one or more of the following:
a. Media pump 180 that helps drive the media addition;
b. Media addition that is controlled at a user-defined rate;
c. One or more user defined flow rates that are monitored and maintained by dual fluid sensor media flow meter system, apparatus or device 170; and
d. Reactor 120 level sensing to prevent reactor 120 volume from meeting or reaching critical levels.

In various embodiments, dual fluid sensor filtrate flow meter system, apparatus or device 240 helps filtrate removal system or stream 130 meet predetermined and/or user defined flow rates. For example, in various embodiments, first filtrate sensor 280 and second filtrate sensor 290 may be used to track movement through filtrate flow or fluid path 150 in filtrate removal system or stream 130. For example, in various embodiments, a length of the filtrate tubing section 300 extending between first filtrate sensor 280 and second filtrate sensor 290 and/or the volume contained in filtrate tubing section 300 extending between first filtrate sensor 280 and second filtrate sensor 290 over that length may be known or determined, and utilized to determine real time flow rates. In various embodiments, filtrate flow valve 270 may be operated to introduce or otherwise allow gas (e.g., air or sterile air) from filtrate flow gas source 260 into filtrate flow or fluid path 150 and ultimately into filtrate tubing section 300. In various embodiments, first filtrate sensor 280 and second filtrate sensor 290 can then each sense or read when a lead line of fluid following the introduced gas passes each of first filtrate sensor 280 and second filtrate sensor 290 and measure or otherwise determine the time that elapses from the moment each sensor 280 and 290 respectively senses the lead line of fluid following the introduced air reaching or passing each sensor 280 and 290. By knowing the interior volume of filtrate tubing section 300 extending between first filtrate sensor 280 and second filtrate sensor 290 (and/or the length of filtrate tubing section 300 extending between first filtrate sensor 280 and second filtrate sensor 290), and the time elapsed between sensing of the lead line by first filtrate sensor 280 and the sensing of the lead line by second filtrate sensor 290, a flow rate may be determined, derived or at least approximated.

In operation, in various embodiments, dual fluid sensor filtrate flow meter system, apparatus or device 240 allows or introduces one or more gas bubbles (e.g., air bubbles) into filtrate flow or fluid path 150 through a sterile gas filter (e.g., by actuating filtrate flow valve 270) and helps track the leading edge of the fluid (behind the gas bubble) as it passes each sensor 280 and 290. For example, in various embodiments, as the leading fluid edge passes first filtrate sensor 280, a filtrate timer is activated and as the leading fluid edge passes second filtrate sensor 290, the filtrate timer may be stopped and read. A known or measured inner diameter of filtrate tubing section 300 and the length of filtrate tubing section 300 between the first and second sensors 280/290 may be determined, fixed or known and correlate or used to approximate or measure a volume. The resulting filtrate timer may be used to determine the actual observed flow rate (e.g., x mL in y sec) and correlated to the filtrate pump 250 setting used for that observed flow rate. Filtrate pump 250 speed adjustments may be made to keep the observed flow rate at, or within a threshold of, a predetermined or user setting. Gas bubbles may later be purged from the filtrate flow or fluid path 150 if required or desired.

It should be appreciated that the sensors (e.g., first and second media sensors 210/220 and/or first and second filtrate sensors 280/290) may also sense other characteristics of the flow through the sensors. For example, each of the sensors may sense the presence of the introduced gas, measure or otherwise determine the time that elapses from the moment each sensor respectively senses the introduced gas reaching or passing each sensor.

Figure 8:
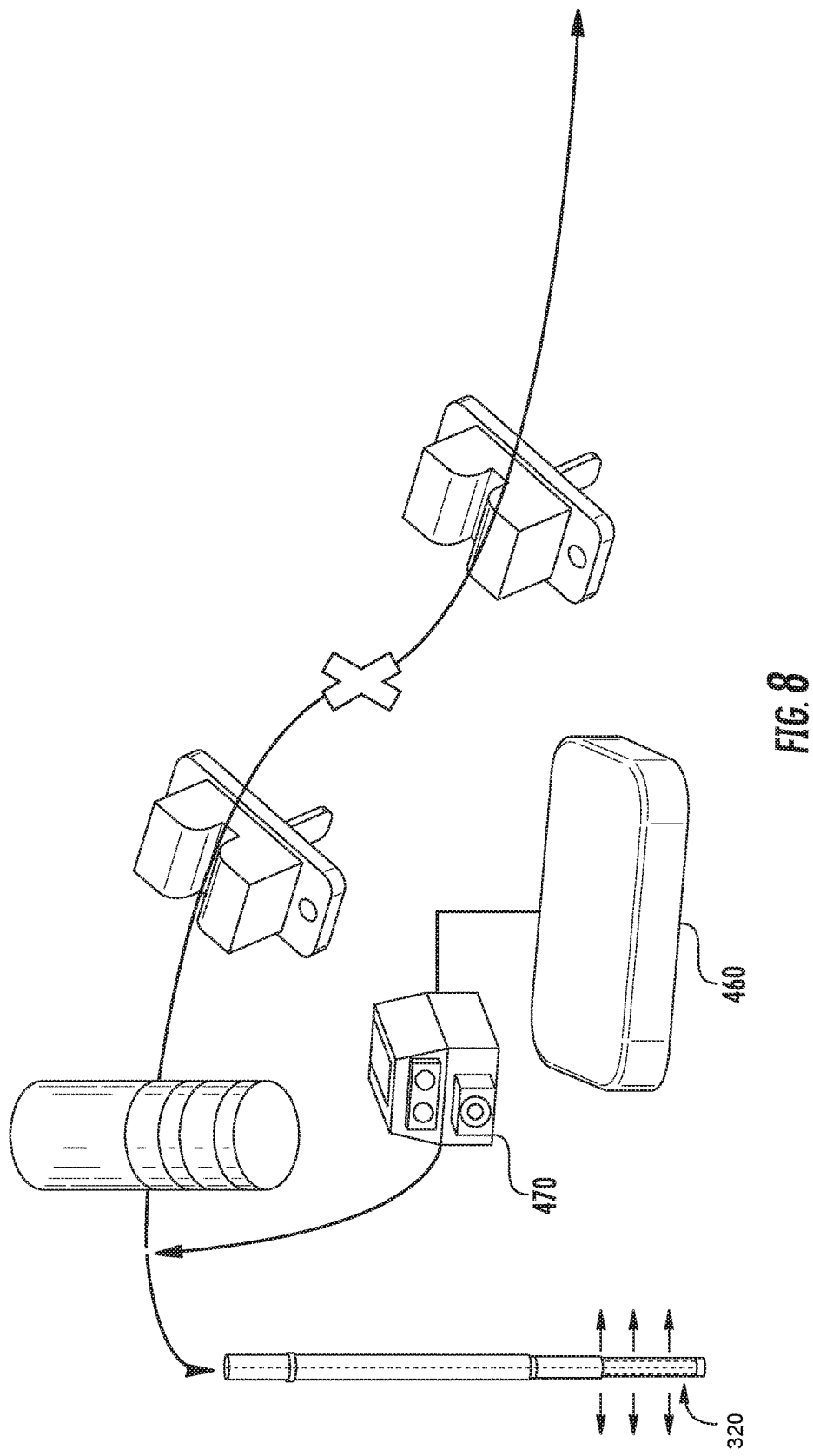
FIG. 8 is a schematic diagram of a filtrate removal system and reactor of the perfusion system of FIG. 1 shown during filtrate back flush according to one or more examples of embodiments.

Referring now to FIGS. 7 and 8, in various embodiments, dual fluid sensor filtrate flow meter system, apparatus or device 240 and/or the condition and observed flow rate through or leaving in-situ filtration probe allows the user to view performance during the perfusion process. As the flow rate of through or leaving in-situ filtration probe 310 (or through filtrate tubing section 150) is observed or measured to be decreasing, the user may program one or more back flush intervals into the control wherein sterile media and/or filtrate can be flushed through membrane 320 to mitigate or otherwise improve reduced flow rates.

For example, and referring now to FIG. 7, an optional back flush option may be programmed into and/or controlled by the controller to mitigate decreased flux of membrane 320. The filtrate removal pump may reverse direction to push filtrate back through in-situ filtration probe 310 and into the reactor. The central control may control back flush intervals (e.g., depending on observed or actual flow rate reduction from in-situ filtration probe 310). The user can define one or more thresholds for when these back flush sequences should occur as well as how much filtrate should be flushed.

As another example, and referring now to FIG. 8, the optional back flush may also occur from a sterile media source (such as a back-flush sterile media source 460) using a back-flush media pump 470), as opposed to, in place of, or in addition to reverse pumping filtrate through the filtration probe as illustrated in FIG. 7. Sterile filtrate or media back flush to mitigate flow reduction may be provided on user defined intervals. Filtration surface or membrane 140 may also be cleaned periodically or continuously by reactor agitation.

In various embodiments, level sensing is employed with the reactor system to ensure critical levels are not met. Minimum fluid levels (e.g., critical minimum fluid levels) and/or maximum critical fluid levels (e.g., critical maximum fluid levels) may be user determined.

Unlike typical or known peristaltic pump driven systems, the disclosed system is able to auto calibrate its flow rates by introduction of sterile air-bubbles into the fluid path. In various embodiments, level sensing is also used in the reactor to create minimum and maximum thresholds to prevent the reactor from running low or high on media.

The disclosed system may be used to automate perfusion for much smaller reactor working volumes than typical or competitive systems. Because typical perfusion systems remove a substantial portion of the reactor volume for cell separation, they are limited on the necessary minimum working volume (e.g., 1 L). The disclosed apparatus and method may work with or on systems as low as 250 mL, or less.

Figure 10:
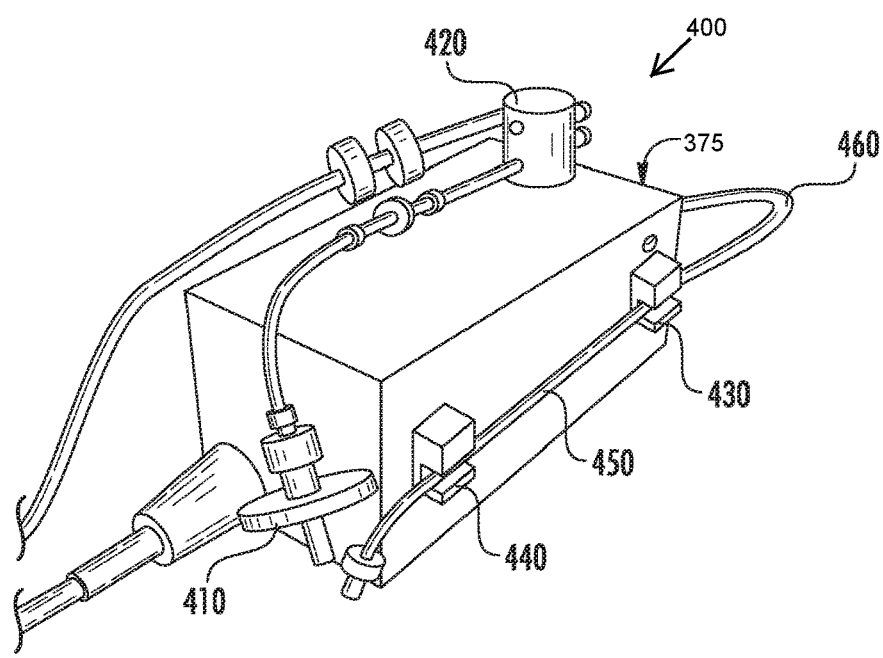
FIG. 10 is a perspective view of a flow monitoring system, according to various examples of embodiments.
Figure 9:
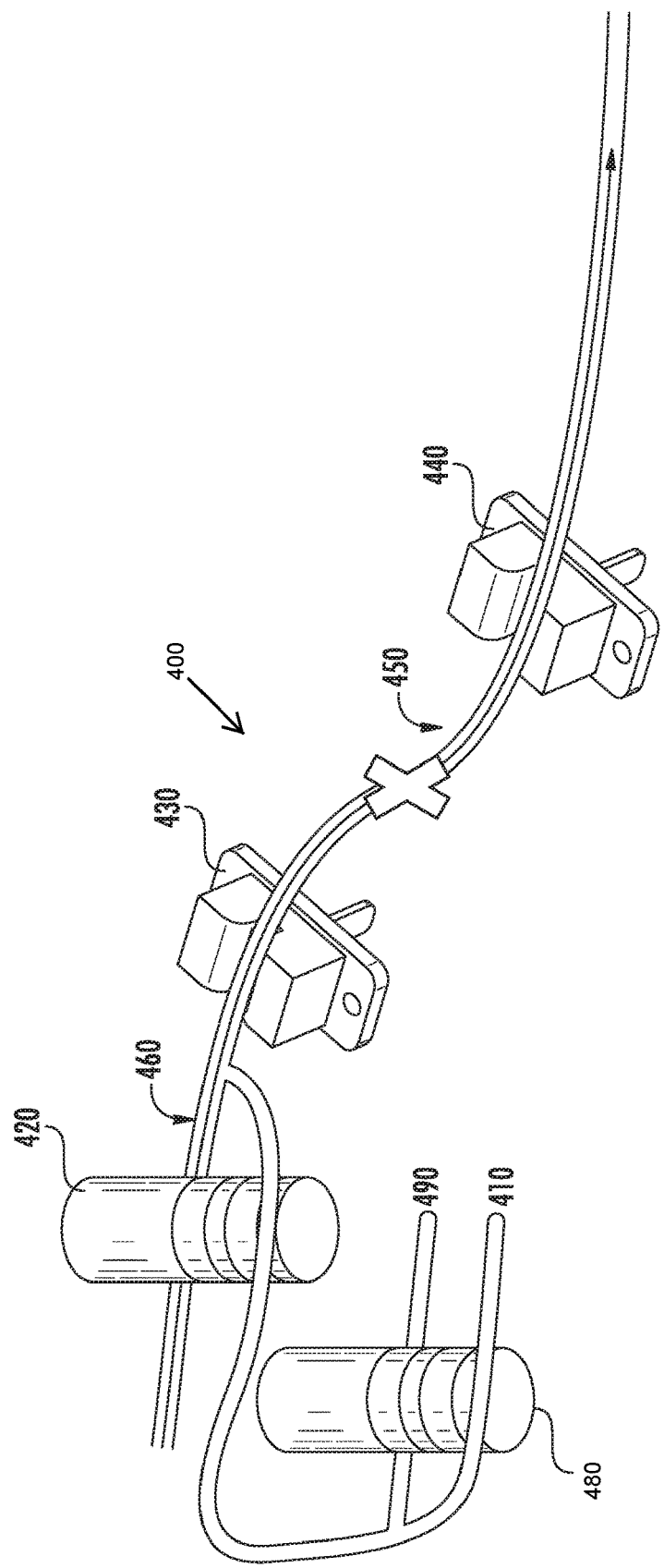
FIG. 9 is a schematic diagram of a flow monitoring system, according to various examples of embodiments.

Referring now to FIGS. 9-10, in various embodiments, a standalone flow meter system, apparatus or device (such as a standalone dual fluid sensor media flow meter system, apparatus or device and/or a standalone dual fluid sensor filtrate flow meter system, apparatus or device) 400 is shown. In various embodiments, the standalone flow meter system, apparatus or device includes a gas source 410 (e.g. a sterile air source), a first flow valve 420 (e.g., a dual pinch valve, a solenoid valve, etc.), a first sensor 430, a second sensor 440, and a media tubing section 450 extending between the first sensor 430 and the second sensor 440. In various embodiments, standalone flow meter system, apparatus or device 400 may be directly welded or otherwise coupled into another or existing fluid path, Standalone flow meter system. apparatus or device 400 may be monitored and/or controlled by a dedicated controller 375 (as shown in FIG, 10).

In operation, in various embodiments, flow meter system, apparatus or device 400 allows or introduces one or more gas bubbles (e.g., air bubbles) into a flow or fluid path 460 through a sterile gas filter (e.g., by actuating first flow valve 420) and helps track the leading edge of the fluid (behind the gas bubble(s)) as it passes each sensor 430 and 440. For example, in various embodiments, as the leading fluid edge passes first sensor 430, a timer (e.g., in controller 375) is activated and as the leading fluid edge passes second sensor 440, the timer may be stopped and read. A known or measured inner diameter of tubing section 450 and the length of tubing section 450 between the first and second sensors 430/440 may be determined, fixed or known, and correlate or used to approximate or measure a volume. The resulting timer may be used to determine the actual observed flow rate (e.g., x mL. in y sec). Gas bubbles may later be purged from media flow or fluid path 460 if required or desired. In various embodiments, controller 375 is similar to controller 360 discussed above.

Referring to FIG. 9, in various embodiments, the standalone flow meter system, apparatus or device 400 also includes a second flow valve 480 (e.g., a dual pinch valve, a solenoid valve, etc.). In various embodiments, second flow valve 480 is coupled to gas source 410 and a cleaning solution source 490. The cleaning solution may be any fluid as desired including water, sterile media, etc. In various embodiments, second flow valve 480 is controlled by controller 375to introduce the cleaning solution into the standalone flow meter system, apparatus or device 400 to help clean valves, tubing and/or connections as needed or desired.

It should be appreciated that the various flow meter systems and methods disclosed herein may also be utilized in other applications including sampling applications. It should also be appreciated that the various flow meter systems and methods may not include a filtration probe or filtered filtrate. In various embodiments, the various flow meter systems and methods are utilized to monitor and/or adjust flows of any fluids or liquids (filtered or unfiltered) and may include other fluid sources or probes (perfusion, sampling, etc.) including dip tubes or sampling ports.

As utilized herein, the terms "approximately," "about," "substantially", and similar terms are intended to have a broad meaning in harmony with the common and accepted usage by those of ordinary skill in the art to which the subject matter of this disclosure pertains. It should be understood by those of skill in the art who review this disclosure that these terms are intended to allow a description of certain features described and claimed without restricting the scope of these features to the precise numerical ranges provided. Accordingly, these terms should be interpreted as indicating that insubstantial or inconsequential modifications or alterations of the subject matter described and claimed are considered to be within the scope of the invention as recited in the appended claims.

It should be noted that any references to relative positions (e.g., "top" and "bottom") in this description are merely used to identify various elements as are oriented in the Figures. It should be recognized that the orientation of particular components may vary greatly depending on the application in which they are used.

For the purpose of this disclosure, the term "coupled" means the joining of two members directly or indirectly to one another. Such joining may be stationary in nature or moveable in nature. Such joining may be achieved with the two members or the two members and any additional intermediate members being integrally formed as a single unitary body with one another or with the two members or the two members and any additional intermediate members being attached to one another. Such joining may be permanent in nature or may be removable or releasable in nature.

It is also important to note that the construction and arrangement of the system, methods, and devices as shown in the various examples of embodiments is illustrative only. Although only a few embodiments have been described in detail in this disclosure, those skilled in the art who review this disclosure will readily appreciate that many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter recited. For example, elements shown as integrally formed may be constructed of multiple parts or elements show as multiple parts may be integrally formed, the operation of the interfaces may be reversed or otherwise varied, the length or width of the structures and/or members or connector or other elements of the system may be varied, the nature or number of adjustment positions provided between the elements may be varied (e.g. by variations in the number of engagement slots or size of the engagement slots or type of engagement). The order or sequence of any process or method steps may be varied or re-sequenced according to alternative embodiments. Other substitutions, modifications, changes and omissions may be made in the design, operating conditions and arrangement of the various examples of embodiments without departing from the spirit or scope of the present inventions.

While this invention has been described in conjunction with the examples of embodiments outlined above, various alternatives, modifications, variations, improvements and/or substantial equivalents, whether known or that are or may be presently foreseen, may become apparent to those having at least ordinary skill in the art. Accordingly, the examples of embodiments of the invention, as set forth above, are intended to be illustrative, not limiting. Various changes may be made without departing from the spirit or scope of the invention. Therefore, the invention is intended to embrace all known or earlier developed alternatives, modifications, variations, improvements and/or substantial equivalents.

I claim:
1. A method for monitoring flow, the method comprising:
   setting an interval during which a pump is run to introduce a flow of sterile media into a reactor;
   running the pump to introduce the flow of sterile media into the reactor;
   introducing an amount of air into the flow of sterile media flowing into the reactor;

sensing, with a first sensor, a first time when a lead line of the flow of sterile media following the amount of air reaches the first sensor;

sensing, with a second sensor, a second time when the lead line of the flow of sterile media reaches the second sensor;

using the first time and the second time to determine a flow rate for the flow of sterile media; and adjusting the interval during which the pump is run based on the determined flow rate for the flow of sterile media.

2. The method of claim 1, wherein the first time and second time are used to determine a flow rate for the flow of sterile media in the tubing by determining an elapsed time between the first time and the second time and comparing a volume of flow of sterile media in the tubing between the first sensor and the second sensor relative to the elapsed time.

3. The method of claim 2, wherein the volume of flow of sterile media is determined from an interior volume of tubing extending between the first sensor and the second sensor.

4. The method of claim 1, wherein the amount of air is introduced into the flow of sterile media through a dual pinch valve.

5. A method for monitoring flow, the method comprising:
running a pump to provide a media flow from a reactor into a tubing;
introducing an amount of air into the media flow;
sensing, with a first sensor, a first time when a lead line of the media flow in the tubing following the amount of air reaches the first sensor;
sensing, with a second sensor, a second time when the lead line of the media flow in the tubing reaches the second sensor;
using the first time and the second time to determine a flow rate for the media flow; and
calibrating, recalibrating or controlling the pump based on the determined flow rate for the media flow from the reactor into tubing and a predefined flow rate of media flow from the reactor into tubing.

6. The method of claim 5, further comprising calibrating, recalibrating or controlling the pump to adjust or compensate when the determined flow rate is less than the predefined flow rate.

7. The method of claim 5, wherein the calibration, recalibration, or control of the pump comprises adjusting an interval during which the pump is run to provide the media flow from the reactor into the tubing.

8. The method of claim 5, further comprising setting a pump interval during which the pump runs to create the media flow from the reactor into the tubing and adjusting the pump interval based on the determined flow rate to obtain a desired volume of media flow from the reactor.

9. A method for monitoring flow, the method comprising:
introducing an amount of air into a fluid flow;
sensing, with a first sensor, a first time when a lead line of the fluid flow following the amount of air reaches the first sensor;
sensing, with a second sensor, a second time when the lead line of the fluid flow reaches the second sensor; and
using the first time and the second time to determine a flow rate for the fluid flow;
introducing an amount of air into a filtrate flow in filtrate tubing running from the reactor;
sensing, with a third sensor, a third time when a lead line of the filtrate flow following the amount of air introduced in the filtrate tubing in reaches the third sensor;
sensing, with a fourth sensor, a fourth time when the lead line of the filtrate flow following the amount of air introduced in the filtrate tubing in reaches the fourth sensor; and
using the third time and the fourth time to determine a flow rate for the filtrate flow in the filtrate tubing.

10. The method of claim 9, further comprising adjusting the flow rate for the fluid flow to be closer to a predetermined flow rate of fluid flow.

11. The method of claim 10, further comprising adjusting the flow rate for the filtrate flow to be closer to a predetermined flow rate of fluid flow.

12. The method of claim 9, further comprising adjusting the flow rate for the filtrate flow to be closer to a predetermined flow rate of fluid flow.

* * * * *